United States Patent
Chen et al.

(10) Patent No.: US 11,524,928 B2
(45) Date of Patent: Dec. 13, 2022

(54) METHOD FOR PREPARATION OF 2,5-DIMETHYLPHENOL BY SELECTIVE CATALYTIC CONVERSION OF LIGNIN

(71) Applicant: Anhui University of Science & Technology, Huainan (CN)

(72) Inventors: Mingqiang Chen, Huainan (CN); Yishuang Wang, Huainan (CN); Zhonglian Yang, Huainan (CN); Jun Wang, Huainan (CN); Han Zhang, Huainan (CN); Jinhui Zhang, Huainan (CN)

(73) Assignee: Anhui University of Science & Technology, Huainan (CN)

( * ) Notice: Subject to any disclaimer, the term of this patent is extended or adjusted under 35 U.S.C. 154(b) by 94 days.

(21) Appl. No.: 17/242,001

(22) Filed: Apr. 27, 2021

(65) Prior Publication Data

US 2022/0298092 A1 Sep. 22, 2022

(30) Foreign Application Priority Data

Mar. 16, 2021 (CN) .......................... 202110280165.9

(51) Int. Cl.
| | | |
|---|---|---|
| *C07C 37/54* | (2006.01) | |
| *B01J 23/88* | (2006.01) | |
| *B01J 37/02* | (2006.01) | |
| *B01J 37/08* | (2006.01) | |
| *C07C 39/07* | (2006.01) | |

(52) U.S. Cl.
CPC ............. *C07C 37/54* (2013.01); *B01J 23/88* (2013.01); *B01J 37/0201* (2013.01); *B01J 37/08* (2013.01); *C07C 39/07* (2013.01); *C07C 2601/16* (2017.05)

(58) Field of Classification Search
CPC ..................................................... C07C 37/54
See application file for complete search history.

(56) References Cited

U.S. PATENT DOCUMENTS

| | | | |
|---|---|---|---|
| 9,534,650 B2 * | 1/2017 | Kuroe .................. C08L 97/005 |
| 2013/0232853 A1 * | 9/2013 | Peterson ................. C07G 1/00 568/426 |

* cited by examiner

*Primary Examiner* — Sikarl A Witherspoon
(74) *Attorney, Agent, or Firm* — Banner & Witcoff, Ltd.

(57) ABSTRACT

The present disclosure discloses a method for preparing 2,5-dimethylphenol by selective catalytic conversion of lignin, relates to the technical field of chemistry, and includes the following steps: mixing lignin, a catalyst, and ethanol, and then carrying out a catalytic conversion reaction of lignin under the gaseous supercritical conditions of ethanol; and cooling the reaction product by quenching after the completion of reaction, and then subjecting it to separation and extraction to obtain 2,5-dimethylphenol. The catalyst comprises a modified sepiolite carrier, an active metal Mo, and auxiliary agents Zr and Fe. The process of the present disclosure is simple, and the prepared catalyst is a solid catalyst, which avoids problems of difficult recovery, serious environmental pollution and equipment corrosion caused by the use of homogeneous organic acid-base catalysts.

10 Claims, No Drawings

METHOD FOR PREPARATION OF 2,5-DIMETHYLPHENOL BY SELECTIVE CATALYTIC CONVERSION OF LIGNIN

CROSS REFERENCE TO RELATED APPLICATIONS

The present application claims foreign priority to Chinese Patent Application No. 202110280165.9, filed Mar. 16, 2021, the disclosure of which is incorporated herein by reference in its entirety.

TECHNICAL FIELD

The present disclosure belongs to the technical field of chemistry, and specifically relates to a method for preparing 2,5-dimethylphenol by selective catalytic conversion of lignin.

BACKGROUND

Lignin is one of the main components of woody biomass, and as a natural aromatic polymer, has great potential in the production of phenolic compounds. The high-value application of lignin is limited because of its complex three-dimensional network structure and chemical heterogeneity, and lignin has been directly discharged as a by-product in the pulp and paper industry for a long time, causing serious waste of resources and environmental pollution.

Lignin can be converted to single-molecule aryl compounds by catalytic means to be used in important fields such as chemical industry, materials, medicines, etc., which can serve as substitutes of fossil products such as petroleum and the like. Lignin is a three-dimensional network of macromolecules interwoven by a large number of aromatic rings through C—O—C and C—C bonds. To realize the utilization of lignin, the key step is to break the complex lignin macromolecules to small molecular fragments, and then further selectively convert them to prepare monomer platform molecules. Studies have found that the directional conversion of lignin can be achieved by the design and preparation of supported metal catalysts with specific bond-breaking functions and the control of key preparation process parameters.

In addition, at present, many substituted phenols are important raw materials and intermediates in the chemical and pharmaceutical industries. In particular, 2,5-dimethylphenol is a raw material for the preparation of trimethylphenol, an intermediate of gemfibrozil and vitamin E, and it is also often used as a disinfectant, solvent, medicine, plasticizer and wetting agent. Currently, methods for synthesizing 2,5-dimethylphenol mainly include sulfonation and alkali fusion method, nitrification reduction method, and direct catalytic hydroxylation method. These methods all cause problems such as fossil raw material consumption, pollutant discharge, and serious equipment corrosion.

Therefore, it is of great significance to the sustainable economic and social development by developing green, efficient, economical and highly selective catalysts, which uses lignin as the raw material, maintains the aromatic ring structure, and at the same time, selectively converts lignin to phenolic monomers to construct a "carbon neutral" raw material system.

SUMMARY

In view of the shortcomings of the prior art, the present disclosure aims to provide a method for preparing 2,5-dimethylphenol by the selective catalytic conversion of lignin to solve the above-mentioned problems in the background art.

The objective of the present disclosure can be achieved by the following technical solutions: a method for preparing 2,5-dimethylphenol by selective catalytic conversion of lignin, comprising the following steps:

Lignin, a catalyst and ethanol are mixed, and then a catalytic conversion reaction of lignin is carried out under the gaseous supercritical conditions of ethanol, After the reaction, the mixture is subjected to cooling by quenching, separation and extraction to obtain 2,5-dimethylphenol, The catalyst comprises a modified sepiolite carrier, an active metal Mo, and auxiliary agents Zr and Fe.

As a further solution of the present disclosure, in the catalyst, the content of the active metal Mo is 20 to 40 wt. %, the content of Zr is 5 to 10 wt. %, the content of Fe is 1 to 5 wt. %, and the remaining is modified sepiolite.

As a further solution of the present disclosure, the modified sepiolite is prepared by a process comprising purifying a sepiolite clay raw material and then subjecting it to a treatment with molten sodium hydroxide, sodium nitrate or sodium chloride.

As a further solution of the present disclosure, the active metals Mo, Zr, and Fe in the catalyst are loaded on the modified sepiolite carrier by impregnation and calcination methods.

As a further solution of the present disclosure, the lignin, catalyst and ethanol are fed in a mass ratio of (1 to 5):(0.1 to 0.5):(35 to 45).

As a further solution of the present disclosure, the conditions of the catalytic conversion reaction are that the temperature is controlled at 280 to 320° C., the reactor is filled with 0.6 to 1.0 MPa high-purity nitrogen, and the reaction time is 4 to 10 hours.

As a further solution of the present disclosure, the separation and extraction steps of 2,5-dimethylphenol are as follows: The reaction product which is cooled by quenching is subjected to a solid-liquid separation to selectively remove excess ethanol in the liquid phase product and water produced during the reaction. Then, a purification solvent is added to the liquid product, and after the product is dissolved, it is subjected to filtration and vacuum variable-temperature distillation to obtain 2,5-dimethylphenol.

As a further solution of the present disclosure, the temperature condition of the vacuum variable-temperature distillation is 50 to 55° C., the rotation speed condition is 130 to 150 r/min, and the purification solvent is ethyl acetate.

The beneficial effects of the present disclosure are as follows: The process of the present disclosure is simple, and the prepared catalyst is a solid catalyst, which avoids problems of difficult recovery, serious environmental pollution and equipment corrosion caused by the use of homogeneous organic acid-base catalysts; besides, the used catalyst is based on green and economical sepiolite clay and transition metal elements as main components, and is prepared by simple modification, impregnation and calcination, which is easy to recover and recycle, and has high lignin conversion rate as well as selectivity and yield of 2,5-dimethylphenol monomers.

DETAILED DESCRIPTION

The technical solutions in the examples of the present disclosure are described clearly and completely hereinbelow. Obviously, the described examples are only a part of the examples of the present disclosure, rather than all the examples. Based on the examples of the present disclosure, all other examples obtained by a person of ordinary skill in the art without doing inventive work shall fall within the protection scope of the present disclosure.

A method for preparing 2,5-dimethylphenol by selective catalytic conversion of lignin, comprising the following steps: mixing lignin, a catalyst, and ethanol, and then carrying out a catalytic conversion reaction of lignin under the gaseous supercritical conditions of ethanol; and cooling the reaction product by quenching after the completion of reaction, followed by separation and extraction to obtain 2,5-dimethylphenol. The catalyst comprises a modified sepiolite carrier, an active metal Mo, and auxiliary agents Zr and Fe.

Preferably, in the catalyst, the content of the active metal Mo is 20 to 40 wt. %, the content of Zr is 5 to 10 wt. %, the content of Fe is 1 to 5 wt. %, and the remaining is modified sepiolite.

Preferably, the modified sepiolite is prepared by a process comprising purifying a sepiolite clay raw material and then subjecting it to a treatment with molten sodium hydroxide, sodium nitrate or sodium chloride.

Preferably, the active metals Mo, Zr, and Fe in the catalyst are loaded on the modified sepiolite carrier by impregnation and calcination methods.

Preferably, the lignin, catalyst and ethanol are fed in a mass ratio of (1 to 5):(0.1 to 0.5):(35 to 45).

Preferably, the conditions of the catalytic conversion reaction are that the temperature is controlled at 280 to 320° C., the reactor is filled with 0.6 to 1.0 MPa high-purity nitrogen, and the reaction time is 4 to 10 hours.

Preferably, the separation and extraction steps of 2,5-dimethylphenol are as follows: The reaction product which is cooled by quenching is subjected to a solid-liquid separation to selectively remove excess ethanol in the liquid phase product and water produced during the reaction. Then, a purification solvent is added to the liquid product, and after the product is dissolved, it is subjected to filtration and vacuum variable-temperature distillation to obtain 2,5-dimethylphenol.

Preferably, the temperature condition of the vacuum variable-temperature distillation is 50 to 55° C., the rotation speed condition is 130 to 150 r/min, and the purification solvent is ethyl acetate.

Preparation of Catalysts

Sepiolite clay, as is, is pickled, calcined, pulverized, and sieved to obtain purified sepiolite powder. The sepiolite powder is mixed with sodium nitrate or sodium hydroxide or sodium chloride in a mass ratio of 5:1, and placed in a tube furnace at 450° C. for constant-temperature calcination for 4 hours. Then, the obtained solids are subjected to washing with deionized water, centrifugal separation, filtration, and drying to obtain a modified sepiolite carrier. An amount of $(NH_4)_6Mo_7O_{24} \cdot 4H_2O$, $Zr(NO_3)_4 \cdot 5H_2O$ and $Fe(NO_3)_3 \cdot 9H_2O$ are weighed and added to 50 mL of ethanol to dissolve completely. Thereafter, 5 g of modified sepiolite carrier is added to the solution, and mixed with stirring at room temperature for 2 hours. The suspension is subsequently transferred into a hydrothermal synthesis reactor and impregnated at a constant temperature of 180° C. for 12 hours, and then the suspension is removed, filtered, dried, ground and calcined in a tube furnace under a reducing atmosphere (10% $H_2/N_2$) at 500° C. for 4 hours to obtain a catalyst, which is denoted as xMo-yZr-zFe/SEP-M (x, y, z are the mass fractions of Mo, Zr, Fe in the catalyst, and SEP-M stands for modified sepiolite Carrier).

By adjusting the addition amount of $(NH_4)_6Mo_7O_{24} \cdot 4H_2O$, $Zr(NO_3)_4 \cdot 5H_2O$ and $Fe(NO_3)_3 \cdot 9H_2O$, a series of xMo-yZr-zFe/SEP-M are prepared, which are 20Mo-5Zr-1Fe/SEP-M, 40Mo-10Zr-5Fe/SEP-M, 30Mo-7Zr-3Fe/SEP-M, 20Mo-6Zr-2Fe/SEP-M, 25Mo-8Zr-5Fe/SEP-M, 35Mo-9Zr-3Fe/SEP-M, and 40Mo-7Zr-3Fe/SEP-M, respectively.

Example 1

Selective Catalytic Conversion of Lignin to 2,5-Dimethylphenol 1.00 g of alkali lignin and 0.10 g of 20Mo-5Zr-1Fe/SEP-M catalyst are added to a 100 mL autoclave; then 35 mL of absolute ethanol is added thereto; and subsequently, the autoclave is filled with 0.6 MPa of high-purity nitrogen. Before reaction, the mixture is stirred at 620 rpm for 15 minutes; then the temperature is raised from room temperature to 280° C. at a temperature rising rate of 6° C./min; and the reaction is carried out at a constant temperature for 4 hours. After the completion of reaction, the autoclave is quickly quenched in an ice water bath. After the temperature is lowered to room temperature, the reaction product is removed and filtered with a sand core funnel to obtain a liquid product, which is then placed in a rotary evaporator. The liquid phase product is dried by evaporation under the conditions of 50° C. and 130 r/min (to remove the ethanol solvent and water phase). Thereafter, ethyl acetate is added to the obtained liquid phase product, and vibrated in an ultrasonic vibrator for 6 minutes. After the completion of dissolution, the solution is removed, and filtered with an organic filter head (to separate insoluble products of ethyl acetate). The resulting filtrate is placed in a distillation flask to evaporate the soluble liquid phase of ethyl acetate at 50° C. and 130 r/min to obtain 2,5-dimethylphenol.

According to calculations, in this example, the lignin conversion rate exceeds 95%, the 2,5-dimethylphenol monomer yield is 250.5 mg/g of lignin, and the selectivity exceeds 42%.

Example 2

5.00 g of alkali lignin and 0.50 g of 40Mo-10Zr-5Fe/SEP-M catalyst are added to a 100 mL autoclave; then 45 mL of absolute ethanol is added thereto; and subsequently, the autoclave is filled with 1.0 MPa of high-purity nitrogen. Before reaction, the mixture is stirred at 620 rpm for 15 minutes; then the temperature is raised from room temperature to 320° C. at a temperature rising rate of 6° C./min; and the reaction is carried out at a constant temperature for 10 hours. After the completion of reaction, the autoclave is quickly quenched in an ice water bath. After the temperature is lowered to room temperature, the reaction product is removed and filtered with a sand core funnel to obtain a liquid product, which is then placed in a rotary evaporator. The liquid phase product is dried by evaporation under the conditions of 55° C. and 150 r/min (to remove the ethanol solvent and water phase). Thereafter, ethyl acetate is added to the obtained liquid phase product, and vibrated in an ultrasonic vibrator for 6 minutes. After the completion of dissolution, the solution is removed, and filtered with an organic filter head (to separate insoluble products of ethyl acetate). The resulting filtrate is placed in a distillation flask to evaporate the soluble liquid phase of ethyl acetate at 55° C. and 150 r/min to obtain 2,5-dimethylphenol.

According to calculations, in this example, the lignin conversion rate is up to 100%, the 2,5-dimethylphenol monomer yield is 341.3 mg/g of lignin, and the selectivity exceeds 51%.

Example 3

3.00 g of alkali lignin and 0.30 g of 30Mo-7Zr-3Fe/SEP-M catalyst are added to a 100 mL autoclave; then 40 mL of absolute ethanol is added thereto; and subsequently, the autoclave is filled with 0.8 MPa of high-purity nitrogen. Before reaction, the mixture is stirred at 620 rpm for 15 minutes; then the temperature is raised from room temperature to 300° C. at a temperature rising rate of 6° C./min; and the reaction is carried out at a constant temperature for 6 hours. After the completion of reaction, the autoclave is quickly quenched in an ice water bath. After the temperature is lowered to room temperature, the reaction product is removed and filtered with a sand core funnel to obtain a liquid product, which is then placed in a rotary evaporator. The liquid phase product is dried by evaporation under the conditions of 52° C. and 140 r/min (to remove the ethanol solvent and water phase). Thereafter, ethyl acetate is added to the obtained liquid phase product, and vibrated in an ultrasonic vibrator for 6 minutes. After the completion of dissolution, the solution is removed, and filtered with an organic filter head (to separate insoluble products of ethyl acetate). The resulting filtrate is placed in a distillation flask to evaporate the soluble liquid phase of ethyl acetate at 52° C. and 140 r/min to obtain 2,5-dimethylphenol.

According to calculations, in this example, the lignin conversion rate is up to 100%, the 2,5-dimethylphenol monomer yield is 356.7 mg/g of lignin, and the selectivity exceeds 55%.

Example 4

2.00 g of alkali lignin and 0.20 g of 20Mo-6Zr-2Fe/SEP-M catalyst are added to a 100 mL autoclave; then 40 mL of absolute ethanol is added thereto; and subsequently, the autoclave is filled with 0.8 MPa of high-purity nitrogen. Before reaction, the mixture is stirred at 620 rpm for 15 minutes; then the temperature is raised from room temperature to 290° C. at a temperature rising rate of 6° C./min; and the reaction is carried out at a constant temperature for 8 hours. After the completion of reaction, the autoclave is quickly quenched in an ice water bath. After the temperature is lowered to room temperature, the reaction product is removed and filtered with a sand core funnel to obtain a liquid product, which is then placed in a rotary evaporator. The liquid phase product is dried by evaporation under the conditions of 54° C. and 140 r/min (to remove the ethanol solvent and water phase). Thereafter, ethyl acetate is added to the obtained liquid phase product, and vibrated in an ultrasonic vibrator for 6 minutes. After the completion of dissolution, the solution is removed, and filtered with an organic filter head (to separate insoluble products of ethyl acetate). The resulting filtrate is placed in a distillation flask to evaporate the soluble liquid phase of ethyl acetate at 54° C. and 140 r/min to obtain 2,5-dimethylphenol.

According to calculations, in this example, the lignin conversion rate is up to 100%, the 2,5-dimethylphenol monomer yield is 336.8 mg/g of lignin, and the selectivity exceeds 48%.

Example 5

2.00 g of alkali lignin and 0.50 g of 25Mo-8Zr-5Fe/SEP-M catalyst are added to a 100 mL autoclave; then 40 mL of absolute ethanol is added thereto; and subsequently, the autoclave is filled with 0.8 MPa of high-purity nitrogen. Before reaction, the mixture is stirred at 620 rpm for 15 minutes; then the temperature is raised from room temperature to 310° C. at a temperature rising rate of 6° C./min; and the reaction is carried out at a constant temperature for 8 hours. After the completion of reaction, the autoclave is quickly quenched in an ice water bath. After the temperature is lowered to room temperature, the reaction product is removed and filtered with a sand core funnel to obtain a liquid product, which is then placed in a rotary evaporator. The liquid phase product is dried by evaporation under the conditions of 54° C. and 140 r/min (to remove the ethanol solvent and water phase). Thereafter, ethyl acetate is added to the obtained liquid phase product, and vibrated in an ultrasonic vibrator for 6 minutes. After the completion of dissolution, the solution is removed, and filtered with an organic filter head (to separate insoluble products of ethyl acetate). The resulting filtrate is placed in a distillation flask to evaporate the soluble liquid phase of ethyl acetate at 54° C. and 140 r/min to obtain 2,5-dimethylphenol.

According to calculations, in this example, the lignin conversion rate is up to 100%, the 2,5-dimethylphenol monomer yield is 316.8 mg/g of lignin, and the selectivity exceeds 45%.

Example 6

2.00 g of alkali lignin and 0.20 g of 35Mo-9Zr-3Fe/SEP-M catalyst are added to a 100 mL autoclave; then 40 mL of absolute ethanol is added thereto; and subsequently, the autoclave is filled with 0.8 MPa of high-purity nitrogen. Before reaction, the mixture is stirred at 620 rpm for 15 minutes; then the temperature is raised from room temperature to 290° C. at a temperature rising rate of 6° C./min; and the reaction is carried out at a constant temperature for 8 hours. After the completion of reaction, the autoclave is quickly quenched in an ice water bath. After the temperature is lowered to room temperature, the reaction product is removed and filtered with a sand core funnel to obtain a liquid product, which is then placed in a rotary evaporator. The liquid phase product is dried by evaporation under the conditions of 54° C. and 140 r/min (to remove the ethanol solvent and water phase). Thereafter, ethyl acetate is added to the obtained liquid phase product, and vibrated in an ultrasonic vibrator for 6 minutes. After the completion of dissolution, the solution is removed, and filtered with an organic filter head (to separate insoluble products of ethyl acetate). The resulting filtrate is placed in a distillation flask to evaporate the soluble liquid phase of ethyl acetate at 54° C. and 140 r/min to obtain 2,5-dimethylphenol.

According to calculations, in this example, the lignin conversion rate is up to 95%, the 2,5-dimethylphenol monomer yield is 236.8 mg/g of lignin, and the selectivity exceeds 48%.

Example 7

2.00 g of alkali lignin and 0.20 g of 40Mo-7Zr-3Fe/SEP-M catalyst are added to a 100 mL autoclave; then 40 mL of absolute ethanol is added thereto; and subsequently, the autoclave is filled with 0.8 MPa of high-purity nitrogen. Before reaction, the mixture is stirred at 620 rpm for 15 minutes; then the temperature is raised from room temperature to 290° C. at a temperature rising rate of 6° C./min; and the reaction is carried out at a constant temperature for 8 hours. After the completion of reaction, the autoclave is quickly quenched in an ice water bath. After the temperature is lowered to room temperature, the reaction product is removed and filtered with a sand core funnel to obtain a liquid product, which is then placed in a rotary evaporator. The liquid phase product is dried by evaporation under the conditions of 54° C. and 140 r/min (to remove the ethanol solvent and water phase). Thereafter, ethyl acetate is added to the obtained liquid phase product, and vibrated in an ultrasonic vibrator for 6 minutes. After the completion of dissolution, the solution is removed, and filtered with an organic filter head (to separate insoluble products of ethyl acetate). The resulting filtrate is placed in a distillation flask to evaporate the soluble liquid phase of ethyl acetate at 54° C. and 140 r/min to obtain 2,5-dimethylphenol.

According to calculations, in this example, the lignin conversion rate is up to 96%, the 2,5-dimethylphenol monomer yield is 266.8 mg/g of lignin, and the selectivity exceeds 40%.

Example 8

In order to further show the progress of the present disclosure, a Ni—W/SiO$_2$ catalyst is prepared by the impregnation and calcination methods of the present disclosure, wherein the mass ratio of Ni/W metals is 1, the total metal content in the catalyst is 40 wt. %, and the remaining is commercially available SiO$_2$. The catalytic conversion reaction of lignin is carried out under the same conditions as described in Example 3. According to calculations, in this example, the lignin conversion rate is less than 80%, the 2,5-dimethylphenol monomer yield is less than 100 mg/g of lignin, and the selectivity is less than 20%.

For a person skilled in the art, it can be understood that various changes, modifications, substitutions, and variations can be made to these examples without departing from the principle and spirit of the present disclosure. Therefore, from any aspect, the examples should be regarded as instructive rather than restrictive. The scope of the present disclosure is defined by the appended claims rather than the above description. The examples are merely preferred examples of the present disclosure, and are not used to limit the present disclosure. Any modifications, equivalent substitutions, improvements, and the like made within the spirit and principle of the present disclosure should be included in the protection scope of the present disclosure.

What is claimed is:

1. A method for preparing 2,5-dimethylphenol by selective catalytic conversion of lignin, comprising the following steps:
   mixing lignin, a catalyst, and ethanol, and then carrying out a catalytic conversion reaction of lignin under the gaseous supercritical conditions of ethanol; and
   cooling the reaction product by quenching after the completion of reaction, followed by separation and extraction to obtain 2,5-dimethylphenol;
   the catalyst comprises a modified sepiolite carrier, an active metal Mo, and auxiliary agents Zr and Fe.

2. The method for preparing 2,5-dimethylphenol by selective catalytic conversion of lignin according to claim 1, wherein in the catalyst, the content of the active metal Mo is 20 to 40 wt. %, the content of Zr is 5 to 10 wt. %, the content of Fe is 1 to 5 wt. %, and the remaining is modified sepiolite.

3. The method for preparing 2,5-dimethylphenol by selective catalytic conversion of lignin according to claim 2, wherein the modified sepiolite is prepared by a process comprising purifying a sepiolite clay raw material and then subjecting it to a treatment with molten sodium hydroxide, sodium nitrate or sodium chloride.

4. The method for preparing 2,5-dimethylphenol by selective catalytic conversion of lignin according to claim 2, wherein the active metals Mo, Zr, and Fe in the catalyst are loaded on the modified sepiolite carrier by impregnation and calcination methods.

5. The method for preparing 2,5-dimethylphenol by selective catalytic conversion of lignin according to claim wherein the lignin, catalyst and ethanol are fed in a mass ratio of (1 to 5):(0.1 to 0.5):(35 to 45).

6. The method for preparing 2,5-dimethylphenol by selective catalytic conversion of lignin according to claim 1, wherein the conditions of the catalytic conversion reaction are that the temperature is controlled at 280 to 320° C., the reactor is filled with 0.6 to 1.0 MPa high-purity nitrogen, and the reaction time is 4 to 10 hours.

7. The method for preparing 2,5-dimethylphenol by selective catalytic conversion of lignin according to claim 1, wherein the separation and extraction steps of 2,5-dimethylphenol are as follows: The reaction product which is cooled by quenching is subjected to a solid-liquid separation to selectively remove excess ethanol in the liquid phase product and water produced during the reaction; then, a purification solvent is added to the liquid product, and after the product is dissolved, it is subjected to filtration and vacuum variable-temperature distillation to obtain 2,5-dimethylphenol.

8. The method for preparing 2,5-dimethylphenol by selective catalytic conversion of lignin according to claim 7, wherein the temperature condition of the vacuum variable-temperature distillation is 50 to 55° C., the rotation speed condition is 130 to 150 r/min, and the purification solvent is ethyl acetate.

9. The method for preparing 2,5-dimethylphenol by selective catalytic conversion of lignin according to claim 2, wherein the lignin, catalyst and ethanol are fed in a mass ration of (1 to 5):(0.1 to 0.5):(35 to 45).

10. The method for preparing 2,5-dimethylphenol by selective catalytic conversion of lignin according to claim 2, wherein the conditions of the catalytic conversion reaction are that the temperature is controlled at 280 to 320° C. the reactor is filled with 0.6 to 1.0 MPa high-purity nitrogen, and the reaction time is 4 to 10 hours.

* * * * *